United States Patent
Strobel et al.

(10) Patent No.: US 7,167,538 B2
(45) Date of Patent: Jan. 23, 2007

(54) EXACT VOLUME IMAGING INVOLVING MULTIPLE PARTIAL SCANS

(75) Inventors: Norbert Karl Strobel, Palo Alto, CA (US); Krishnakumar Ramamurthi, Baltimore, MD (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 31 days.

(21) Appl. No.: 11/091,992

(22) Filed: Jun. 27, 2005

(65) Prior Publication Data

US 2005/0226392 A1    Oct. 13, 2005

Related U.S. Application Data

(60) Provisional application No. 60/557,475, filed on Mar. 30, 2004.

(51) Int. Cl.
*A61B 6/03* (2006.01)
(52) U.S. Cl. ...................................................... 378/17
(58) Field of Classification Search .................. 378/4, 378/15, 17, 196, 197, 198
See application file for complete search history.

(56) References Cited

U.S. PATENT DOCUMENTS

| | | | | |
|---|---|---|---|---|
| 5,278,884 A | * | 1/1994 | Eberhard et al. | 378/4 |
| 5,357,429 A | * | 10/1994 | Levy | 378/17 |
| 5,574,763 A | * | 11/1996 | Dehner | 378/17 |
| 5,802,134 A | | 9/1998 | Larson et al. | |
| 5,999,587 A | * | 12/1999 | Ning et al. | 378/4 |
| 6,075,836 A | * | 6/2000 | Ning | 378/98.12 |
| 6,229,869 B1 | * | 5/2001 | Hu | 378/4 |
| 6,400,791 B1 | * | 6/2002 | Schwarz | 378/17 |
| 6,580,777 B1 | * | 6/2003 | Ueki et al. | 378/17 |
| 7,020,236 B1 | * | 3/2006 | Shechter | 378/17 |
| 7,062,007 B1 | * | 6/2006 | Morita | 378/17 |
| 2002/0141628 A1 | | 10/2002 | Bruder et al. | |
| 2005/0207526 A1 | * | 9/2005 | Altman | 378/20 |

\* cited by examiner

*Primary Examiner*—Allen C. Ho

(57) ABSTRACT

A method for performing an exact volume imaging with a C-arm digital x-ray imaging system by moving the source through two partial circular scans which form a complete source trajectory. The partial circular scans form a complete source trajectory when the plane defined by the C-arm is repositioned for the second scan at an angle equal to the cone angle with respect to the long axis of the patient.

1 Claim, 6 Drawing Sheets

US 7,167,538 B2

EXACT VOLUME IMAGING INVOLVING MULTIPLE PARTIAL SCANS

PRIORITY CLAIM

This application claims priority under 35 U.S.C. 120 to Provisional Application No. 60/557,475 filed on Mar. 30, 2004, entitled "Volume Imaging Involving Multiple Partial Scans", which is hereby incorporated by reference in its entirety.

BACKGROUND OF THE INVENTION

1. Field of the Invention

This invention relates generally to x-ray imaging systems with a C-arm which can be used for volume imaging. More specifically, this invention relates to scanning methods and algorithms used for volume reconstruction.

2. Background and Prior Art

Digital x-ray systems include C-arm volume imaging systems. These C-arm imaging systems have a source and detector that are 180 degrees opposite of each other at the ends of a C-arm. The C-arm itself is capable of being translated along the axis of the patient (the z-axis) (or the patient table can be translated) and capable of being rotated about that axis. The x-ray sources of these C-arm imaging systems can be modeled as projecting a cone of x-ray radiation through a volume of a patient to be detected by a detector having an area.

These C-arm imaging systems have been used to generate three dimensional reconstructions of volumes within patients. Such C-arm imaging systems usually rely on partial circle scans over an angular interval for 180 degrees plus the cone angle within a single plane. This angular interval typically ranges up to 200 degrees. Such a trajectory can exactly reproduce a disk with radius r inside the mid-plane define by the rotation of the line between the source and the detector center. However the volume outside the mid-plan only provides enough information for an approximate reconstruction.

In order to provide an exact reconstruction of an arbitrary volume within a patient, a complete source trajectory is required. A particular complete source trajectory can be seen in FIG. 1. as a "wobble." Various other source trajectories have been combined to provide composites which are complete source trajectories and are well known in the art. Examples include a circle and line, two orthogonal circles, a circle and an arc, and a number of other trajectories which involve moving the source in a number of different dimensions. Once projections have been acquired over a complete source trajectory, an appropriate beam reconstruction algorithm can be used a known in the art.

However, the above complete source trajectories are impractical to achieve with the current C-arm imaging systems. Further it is preferable that the source move with a constant speed. This avoids significant complications in implementing the reconstruction algorithm. Accordingly, there remains a need in the art for a complete source trajectory which can be practically implemented in current C-arm x-ray imaging systems.

SUMMARY OF THE INVENTION

A method for performing an exact volume imaging with a C-arm digital x-ray imaging system by moving the source through two partial circular scans which form a complete source trajectory. The partial circular scans form a complete source trajectory when the plane defined by the C-arm is repositioned for the second scan at an angle equal to the cone angle with respect to the long axis of the patient.

BRIEF DESCRIPTION OF THE DRAWINGS

The present invention will become more fully understood from the detailed description given herein below and the accompanying drawings which are given by way of illustration only, and are not limitative of the present invention, and wherein.

DETAILED DESCRIPTION OF THE PREFERRED EMBODIMENTS

Figure 1:
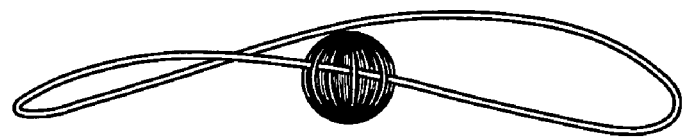
FIG. 1 is the graph of a wobble complete source trajectory.
Figure 2:
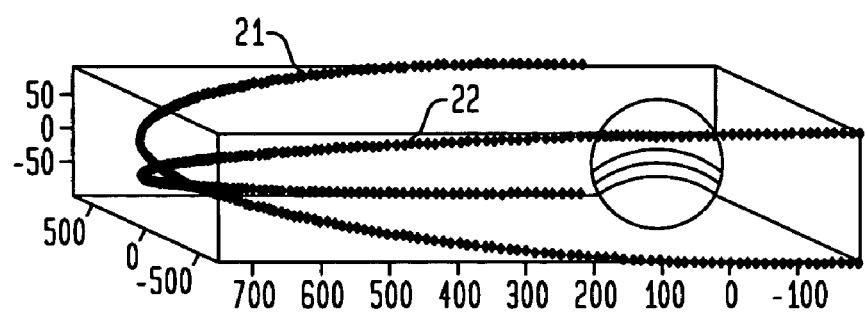
FIG. 2 is a graph of two source trajectories which when combined form a complete source trajectory.

According to the present invention, a method for providing a complete source trajectory to achieve an exact reconstruction of a scan field of view is provided. See FIG. 2. In essence, a first partial circle scan is used for source trajectory 21, and then the plane of the C-arm is rotated at an angle to the z-axis. Then a second partial circle scan 22 is performed. Together these constitute a complete source trajectory. Such a complete source trajectory can be completed with current C-arm systems and at constitute source speed. The angle between the planes defined by the two partial (or short) circle scans is $\beta$. The angle of the cone from the source to encompass a volume r within or partially within the patient is the the angle $\beta_{cone}$. According to the present invention, $\beta = \beta_{cone}$.

Figure 3:
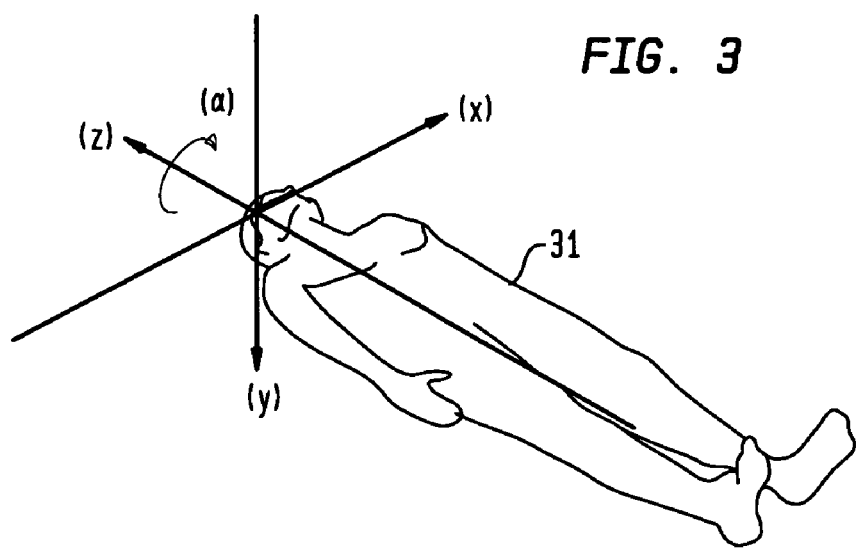
FIG. 3 is a diagram of a patient defining a coordinate system and angles.
Figure 4:
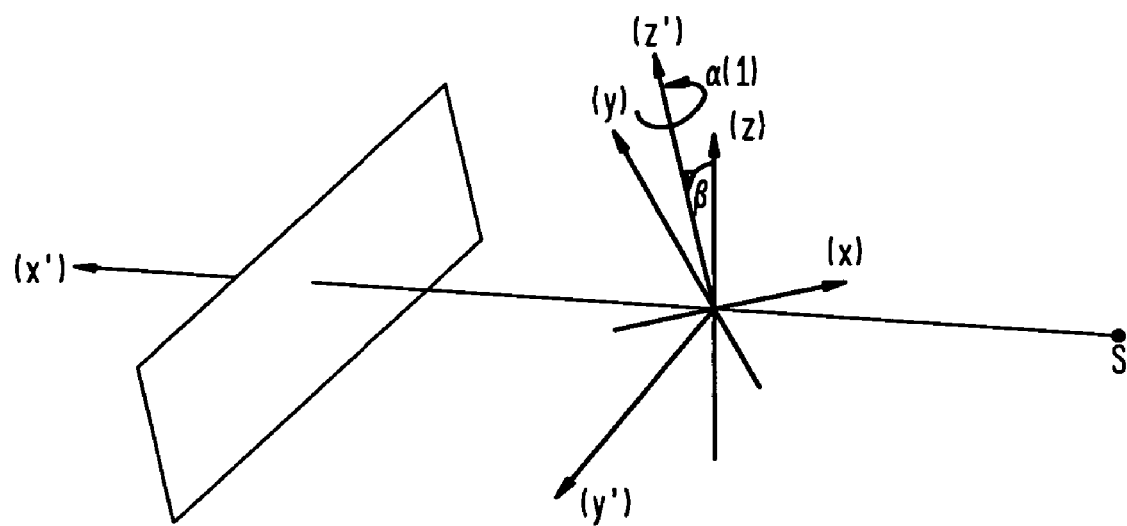
FIG. 4 is a diagram of a coordinate system defined by a source and a detector.
Figure 5A:
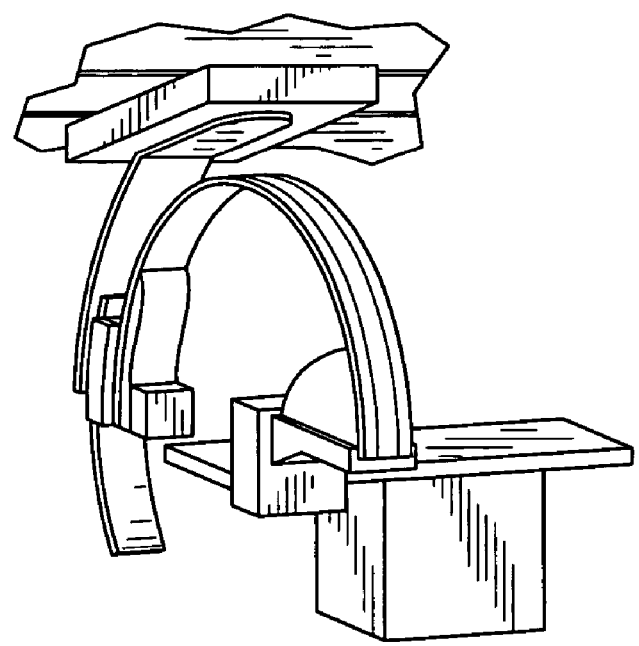
FIG. 5(a)–5(d) are successive views in time of a C-arm imaging system performing a first scan.
Figure 5B:
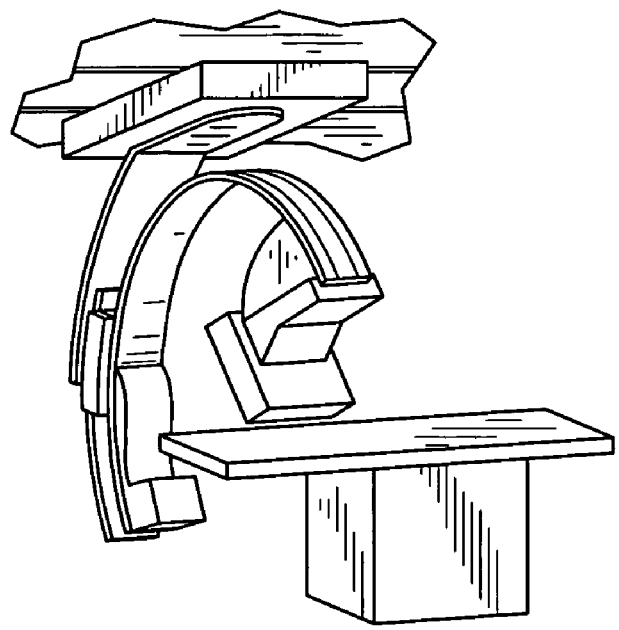
Figure 5C:
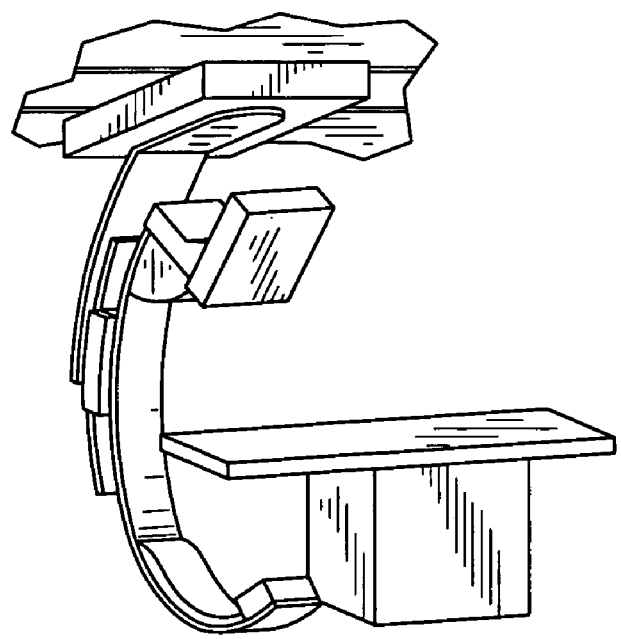
Figure 5D:
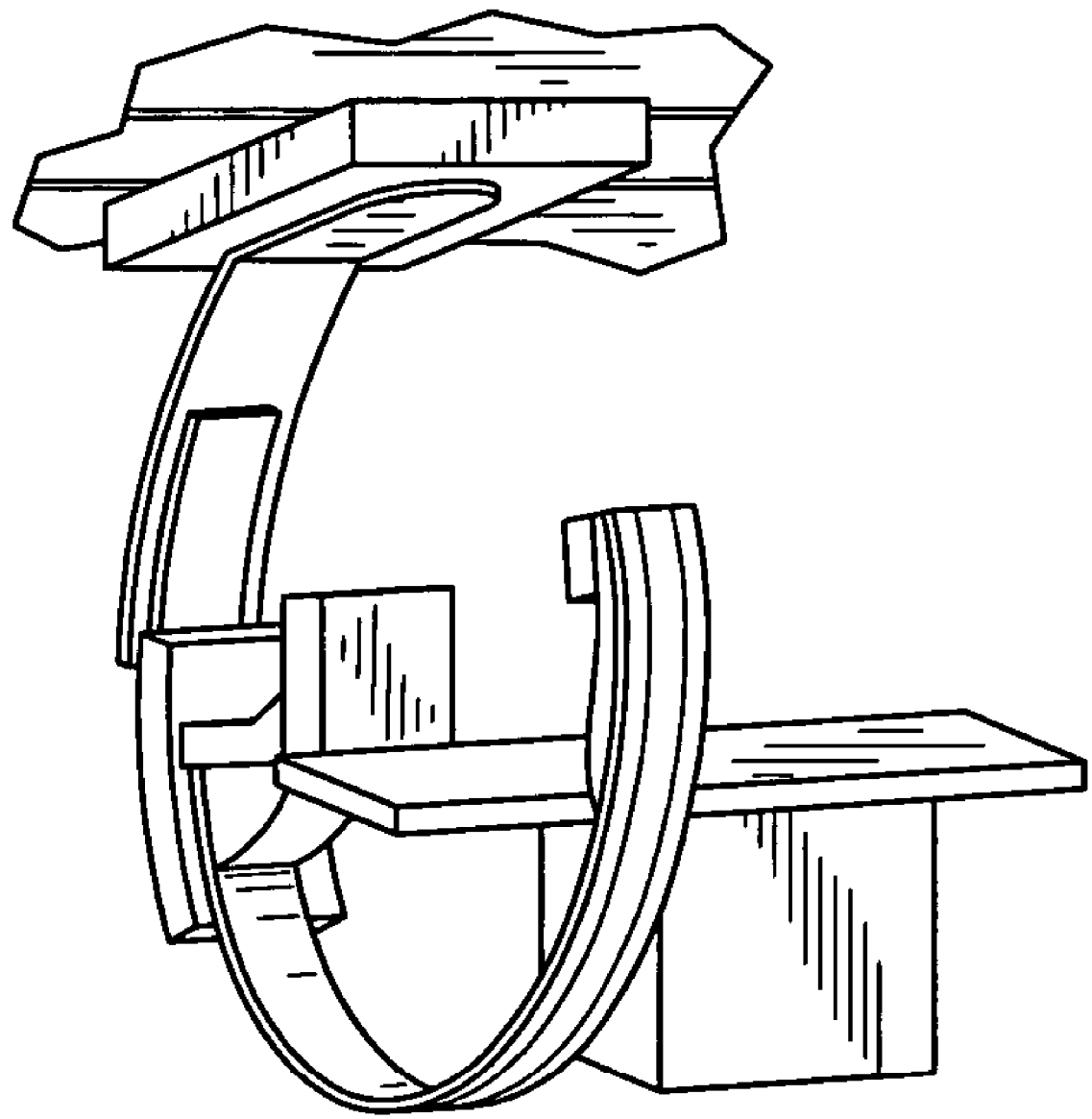
Figure 6A:
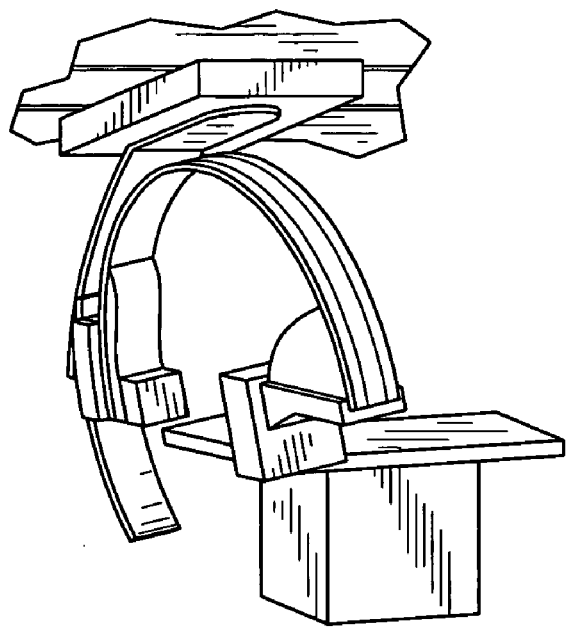
FIG. 6(a)–6(d) are successive views in time of a C-arm imaging system performing a second scan.
Figure 6B:
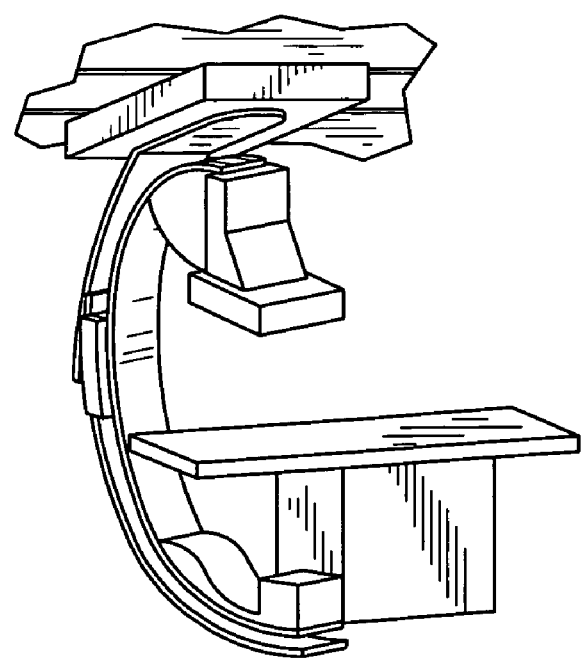
Figure 6C:
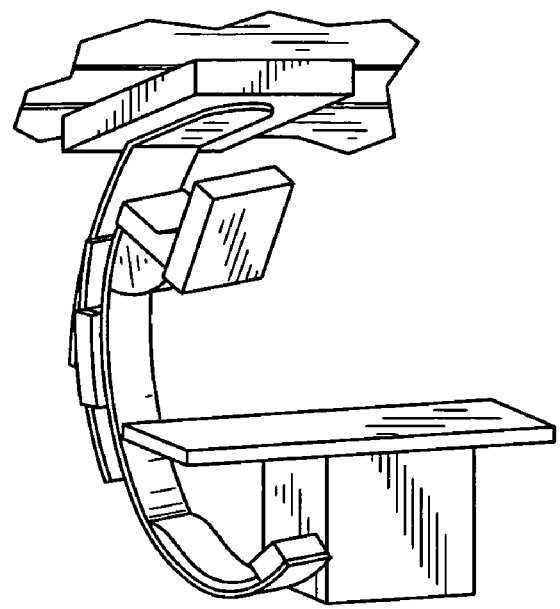
Figure 6D:
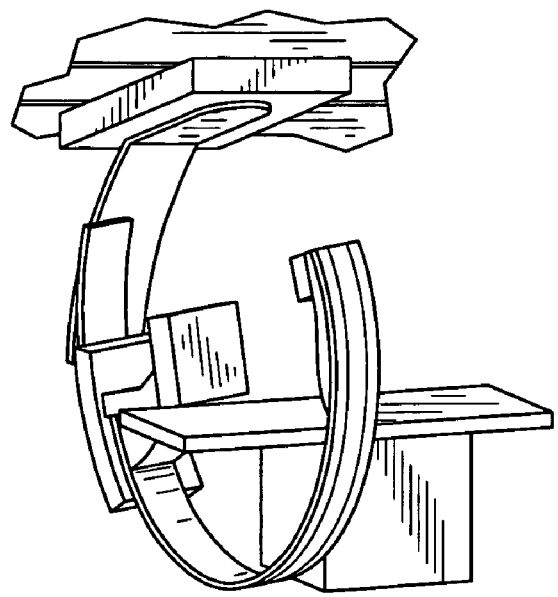

FIG. 3 defines the x,y,z coordinates and the $\beta$ angle with respect to a patient body 31. FIG. 4 defines the angle $\beta$. where the z,y,z and x',y',z' represent the two coordinate systems created by the rotation of angle $\beta$.

According to the present invention, the angle rotated by the source $\beta$ must define a partial circle. More particularly, to achieve an exact reconstruction a must finish at 180 degree+$\beta_{cone}$. Note, however, even a scan for a rotation less than this value if repeated at an angle $\beta_{cone}$ from the z-axis provides a more complete reconstruction than a full rotation a without the second scan at an angle.

More precisely, looking to FIG. 4, we candefine the source trajectory as $$\vec{s} = -D\cos(\alpha)\cos(\beta)\vec{e}_x - D\sin(\alpha)\vec{e}_y + D\cos(\alpha)\sin(\beta)\vec{e}_z,$$

where D is the distance to source.

The above has assumed that the angle with the Z axis of the patient body starts at zero. However, as a more general proposition, as long as the angle between the two plans formed by the two partial circular scans is $\beta_{cone}$ or greater, the initial start position can vary. Particularly where $\beta_{cone}$ is large, the initial scan may need to start at angle for $-\beta_{cone}/2$, with the second scan at $+\beta_{cone}/2$.

In an embodiment of the present invention, a sequence of steps of steps is performed. The C-arm is placed in a start position, with $\alpha=\alpha_{start}$ and $\beta=0°$. A scan is performed where $\alpha$ goes from $\alpha_{start}$ to $\alpha_{start}+180°+\beta_{cone}$. See FIG. 5. Then $\beta$ is set to $\beta_{cone}$ and $\alpha$ reset to a new $\alpha_{start}$. Then $\alpha$ goes from $\alpha_{start}$ to $\alpha_{start}+180°+\beta_{cone}$ again. Normal reconstruction algorithms can now be applied. See FIG. 6.

The invention having been thus described, it will be obvious to those skilled in the art that the same may be varied in many ways without departing from the spirit and scope of the invention.

What is claimed is:

1. A method for obtaining an exact three-dimensional reconstruction of a volume within a patient with C-arm digital x-ray imaging system having a C-arm with an x-ray source at one end and an x-ray detector at the other, comprising the steps of:

defining a cone angle for the volume to be reconstructed;

defining a plane by the source, the C-arm and the detector;

positioning the C-arm such that the plane is orthogonal to the long axis of the patient;

performing a partial circular scan wherein the source rotates by 180 degrees plus the value of the cone angle;

repositioning the C-arm such that the plane forms an angle equal to the cone angle with the long axis;

performing a partial circular scan wherein the source rotates by 180 degrees plus the value of the cone angle; and calculate the reconstructed volume.

* * * * *

UNITED STATES PATENT AND TRADEMARK OFFICE
CERTIFICATE OF CORRECTION

| | | |
|---|---|---|
| PATENT NO. | : 7,167,538 B2 | |
| APPLICATION NO. | : 11/091992 | |
| DATED | : January 23, 2007 | |
| INVENTOR(S) | : Strobel et al. | |

It is certified that error appears in the above-identified patent and that said Letters Patent is hereby corrected as shown below:

Title page, item (22) filing date should read as follows:
      Filed: March 29, 2005

Signed and Sealed this

Twenty-second Day of May, 2007

JON W. DUDAS
*Director of the United States Patent and Trademark Office*